//	United States Patent [19]

Haynes

[11] 4,240,029
[45] Dec. 16, 1980

[54] APPARATUS FOR COUNTING PARTICLES IN A LIQUID SUSPENSION

[75] Inventor: John L. Haynes, Redwood City, Calif.

[73] Assignee: Becton Dickinson & Company, Rutherford, N.J.

[21] Appl. No.: 31,770

[22] Filed: Apr. 20, 1979

Related U.S. Application Data

[63] Continuation-in-part of Ser. No. 780,402, Mar. 23, 1977, Pat. No. 4,165,484.

[51] Int. Cl.³ ............................................. G01R 27/22
[52] U.S. Cl. .......................... 324/71 CP; 235/92 PC
[58] Field of Search ............... 324/71 CP; 235/92 PC

[56] References Cited

U.S. PATENT DOCUMENTS

| 2,656,508 | 10/1953 | Coulter | 324/71 CP |
| 4,110,604 | 8/1978 | Haynes et al. | 235/92 R X |
| 4,165,484 | 8/1979 | Haynes | 324/71 CP |

Primary Examiner—Alfred E. Smith
Assistant Examiner—Thomas P. O'Hare
Attorney, Agent, or Firm—Flehr, Hohback, Test, Albritton & Herbert

[57] ABSTRACT

Apparatus for counting platelets and red blood cells in a whole blood sample includes an aperture type transducer. Alarm techniques are provided for indicating defects in the counting procedure due to excessive noise or red cell fragments, small (microcytic) red cells, and giant (macro) platelets.

9 Claims, 15 Drawing Figures

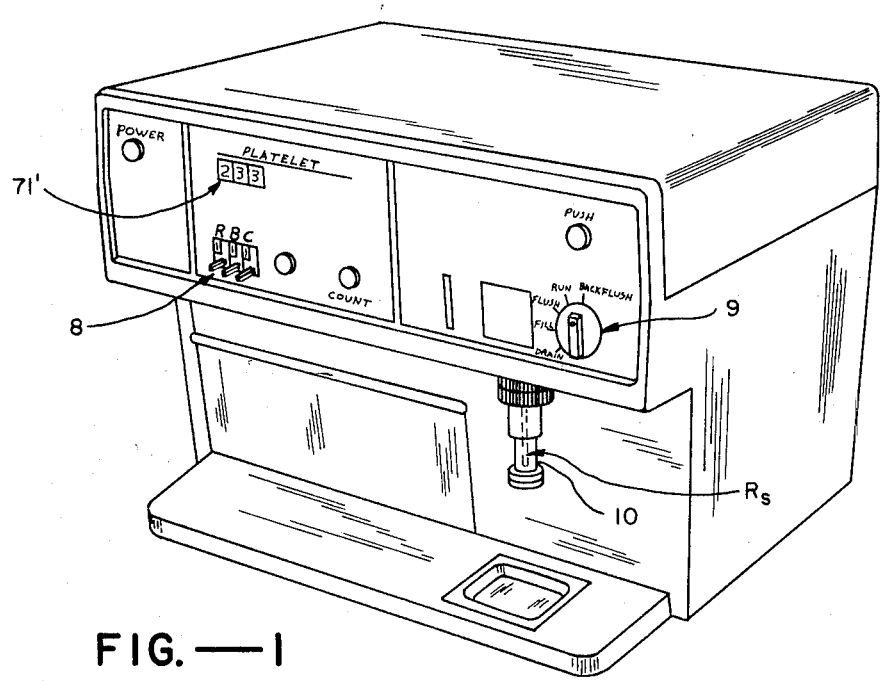
FIG.—1
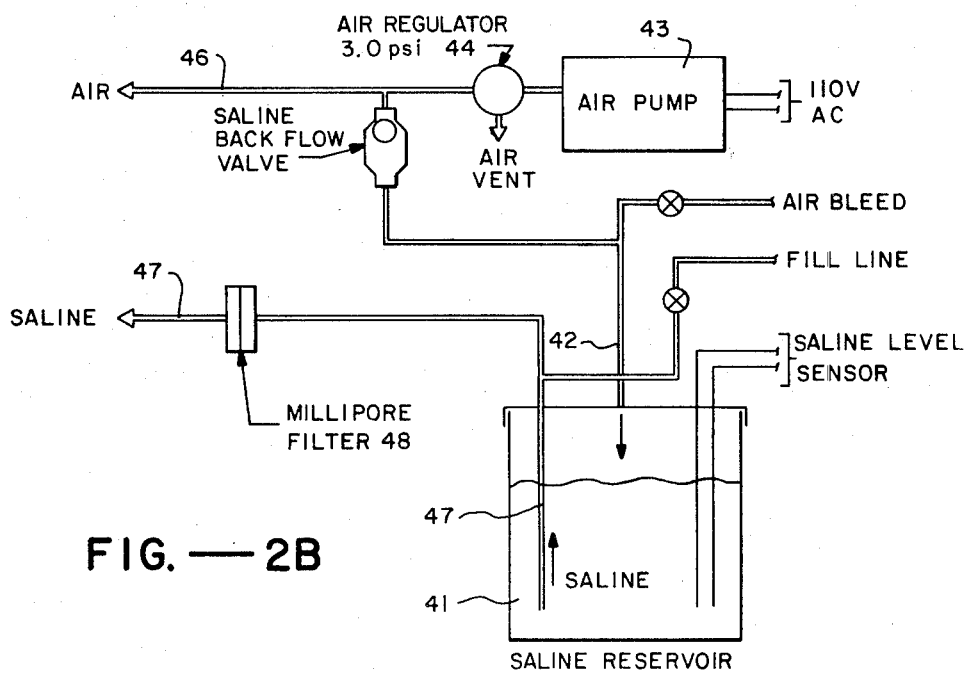
FIG.—2B

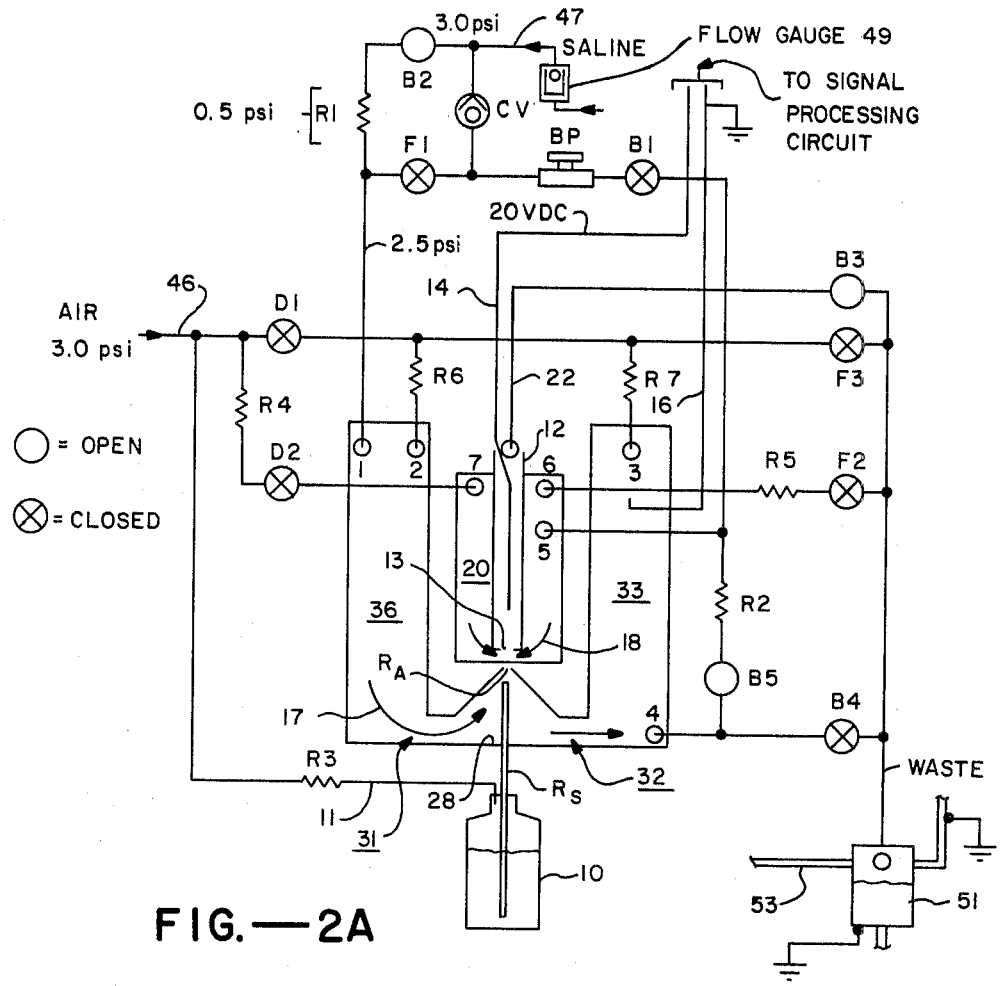
FIG.—2A
| | B1 | B2 | B3 | B4 | B5 | F1 | F2 | F3 | D1 | D2 |
|---|---|---|---|---|---|---|---|---|---|---|
| DRAIN | X | X | O | O | X | X | X | X | O | O |
| FILL | O | — | X | X | X | O | O | O | X | X |
| FLUSH | O | — | O | O | X | O | X | X | X | X |
| RUN | X | O | O | X | O | X | X | X | X | X |
| B. FLUSH | O | X | X | O | O | X | X | X | X | X |
O = OPEN
X = CLOSED
FIG.—2C

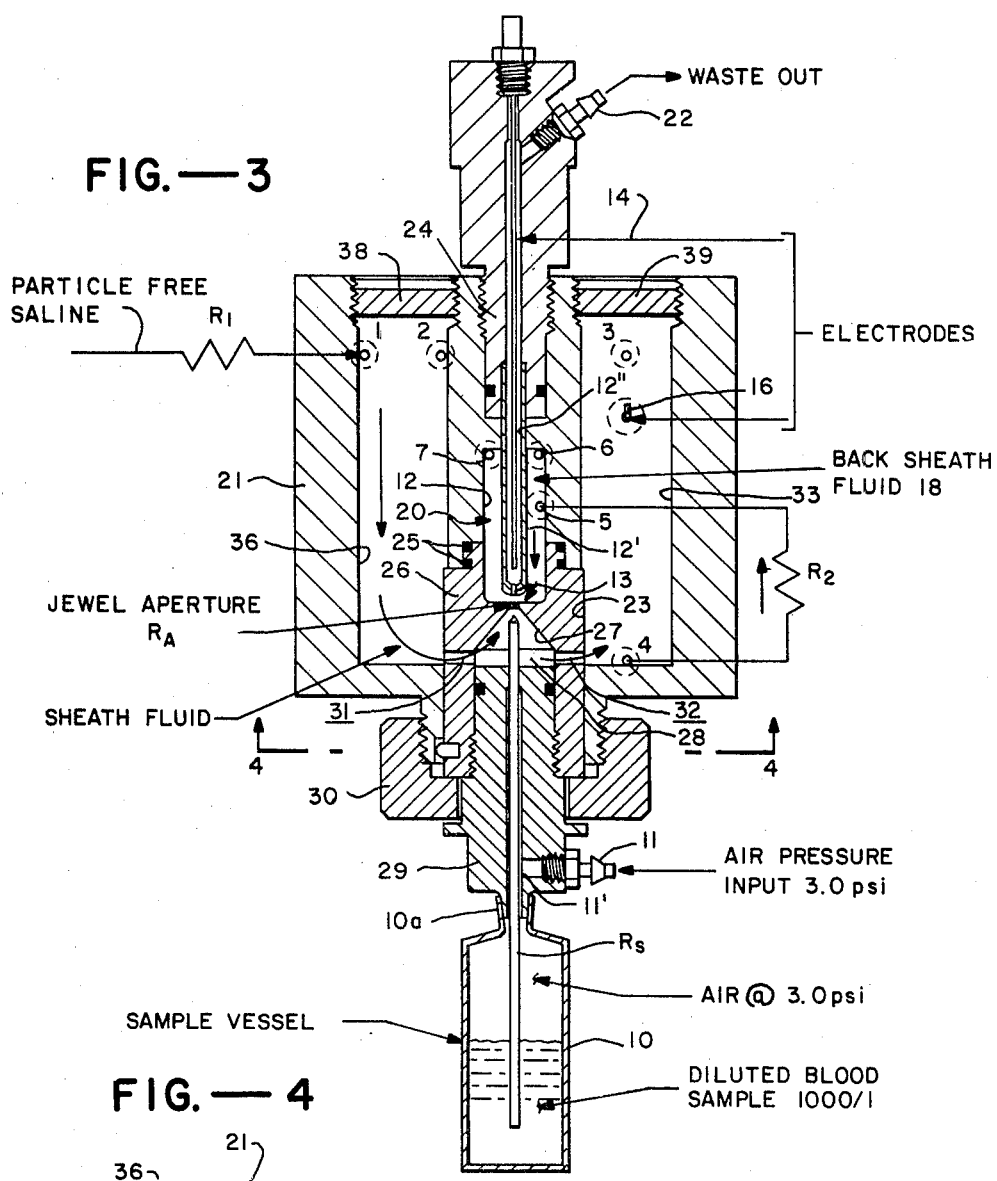
FIG.—3
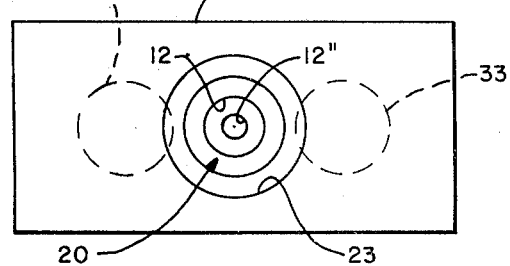
FIG.—4
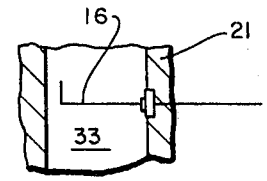
FIG.—3A

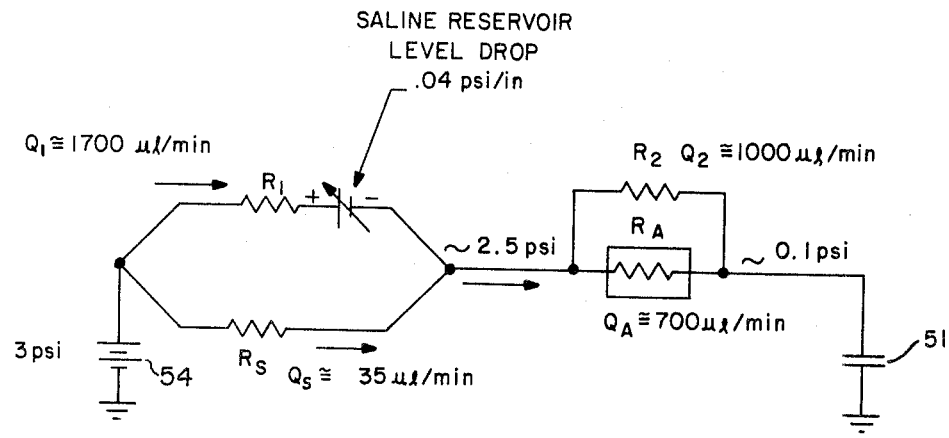
FIG.—5
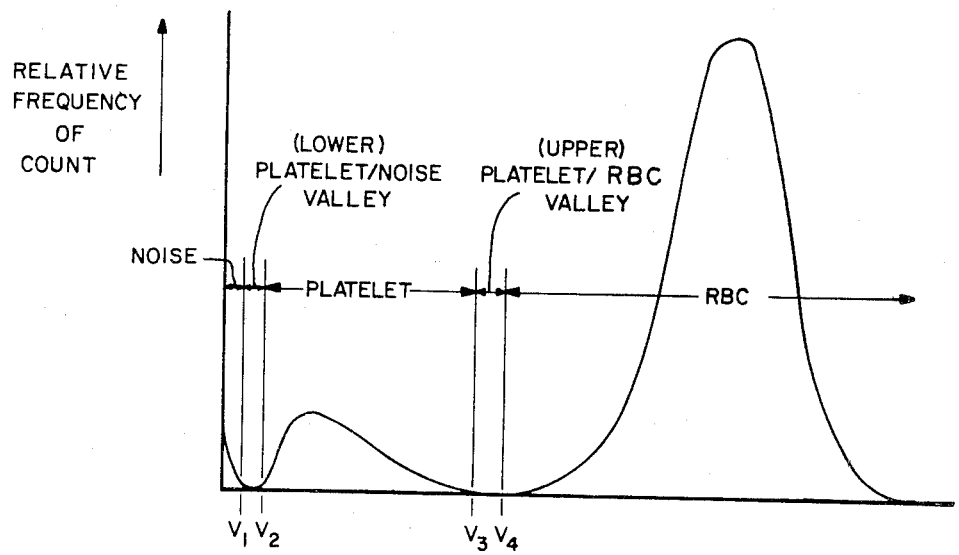
FIG.—8

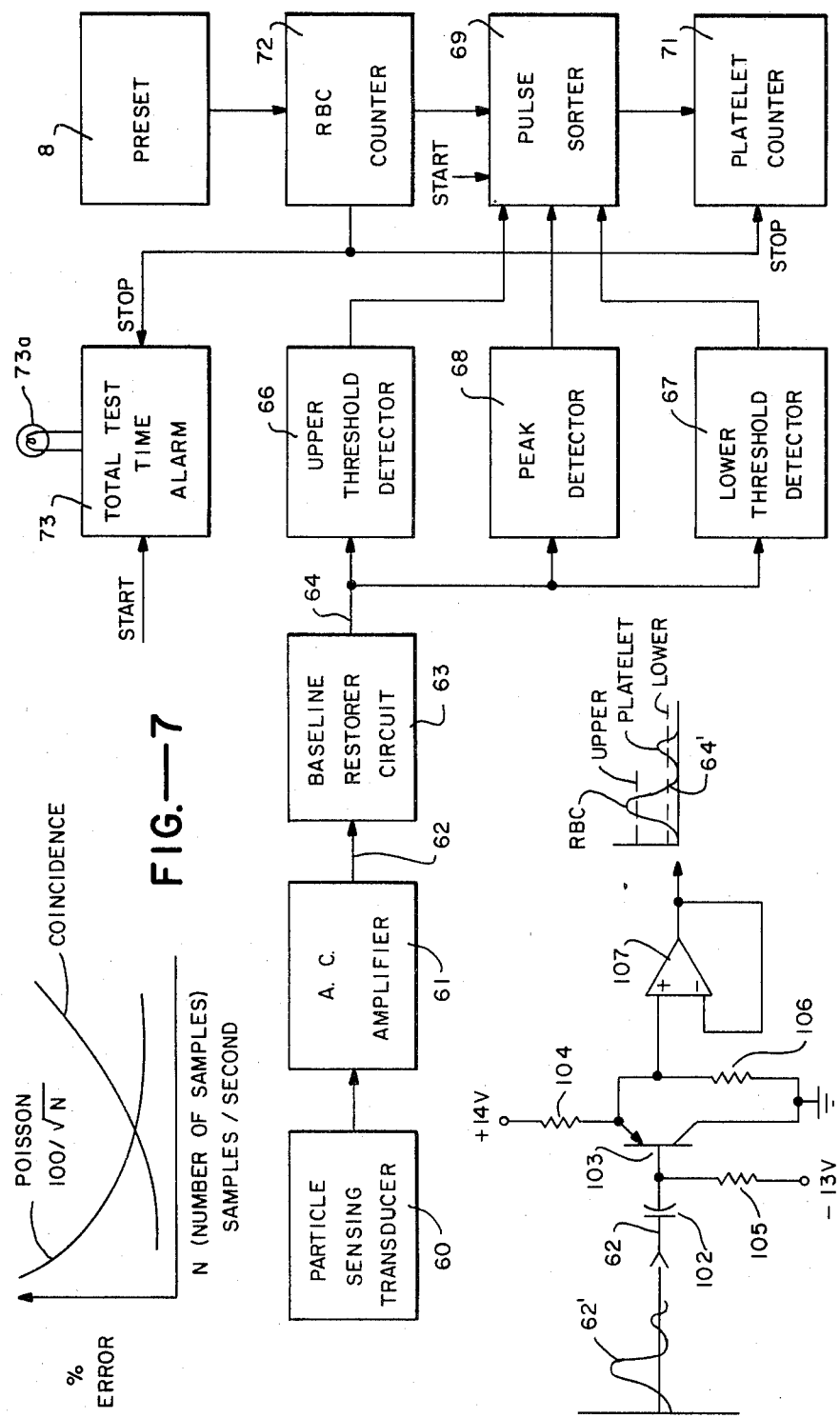

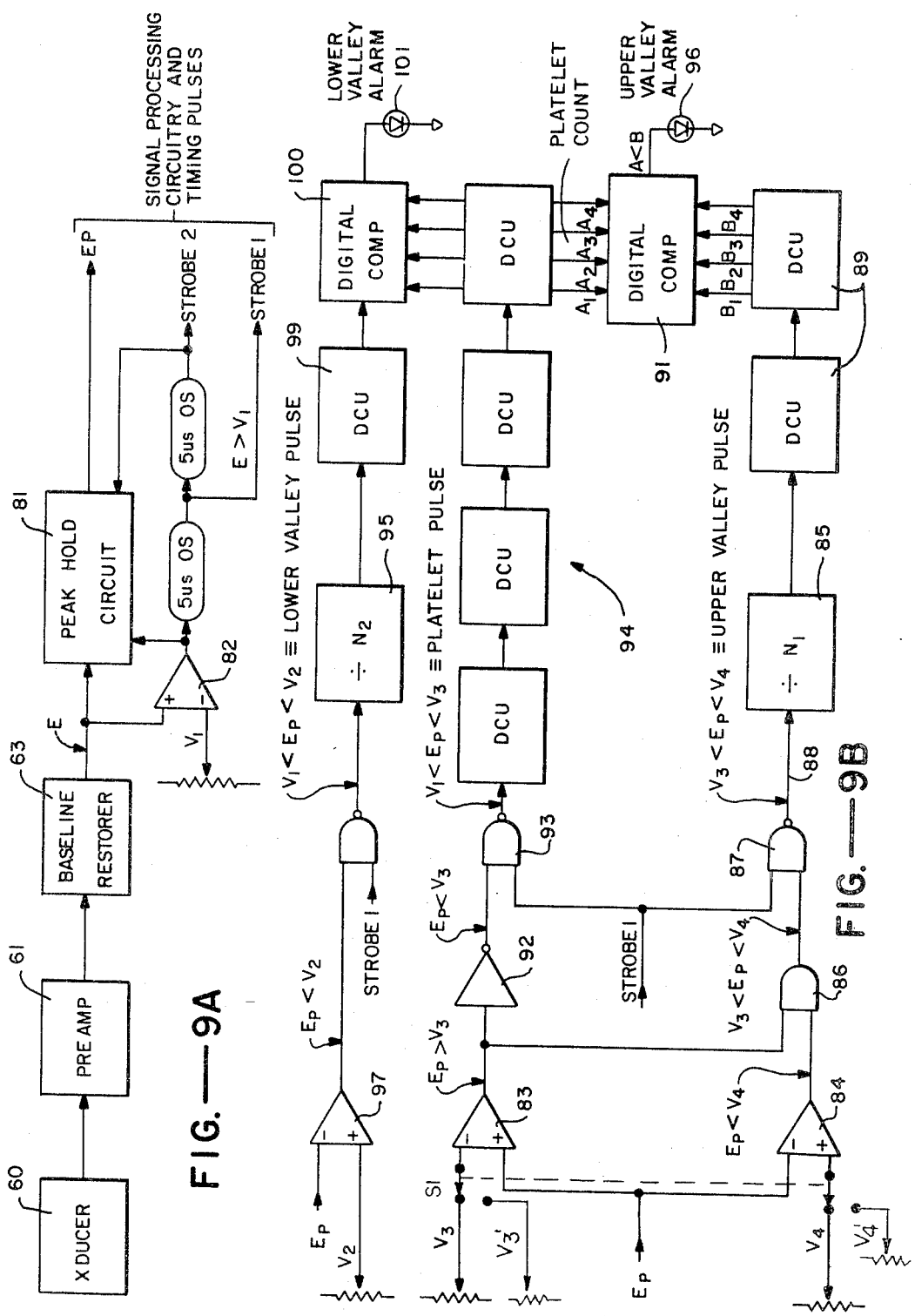
FIG.—9A
FIG.—9B

INCREASED FREQUENCY OF SMALL ERTHROCYTES

INCREASED FREQUENCY OF "GIANT" PLATELETS

APPARATUS FOR COUNTING PARTICLES IN A LIQUID SUSPENSION

The present invention is a continuation in part of Ser. No. 780,402 filed Mar. 23, 1977 and now U.S. Pat. No. 4,165,484, issued Aug. 21, 1979 of John L. Haynes for APPARATUS FOR COUNTING PARTICLES IN A LIQUID SUSPENSION, and relates to an apparatus for counting particles in a liquid suspension and more specifically to alarm techniques for indicating defects in the procedure for counting both red blood cells and platelets in whole blood.

In U.S. Pat. No. 4,110,604, entitled PARTICLE DENSITY MEASURING SYSTEM in the names of the present inventor and Bernard A. Shoor, a technique is disclosed for determining the number of platelets per unit volume of a blood sample by the use of a ratio method which is used in the present invention.

It is an object of the present invention to provide an improved apparatus for counting particles in a liquid suspension.

It is a more specific object to provide alarm techniques for indicating defects in the above counting procedure.

In accordance with the above objects there is provided an apparatus for counting platelets and red blood cells in a sample of blood. This apparatus comprises a means for separately counting platelets and red blood cells of the blood sample, and includes a means for sensing their relative sizes by the magnitude of electrical pulses from an aperture type transducer having an assumed noise level. The platelets have normal lower and upper limits of size distribution, and the red blood cells have a normal lower limit of size distribution. The first voltage means of the transducer is set at approximately the upper limit of the assumed noise level of the transducer. The second voltage reference means is set at approximately the lower limit of normal platelet pulses. The third voltage reference means is set above the upper limit of normal platelet pulses. The fourth voltage reference means is set below the lower limit of normal red blood cell pulses. The apparatus also contains a means for counting electrical pulses greater than the first voltage reference but less than the second voltage reference, which compares these counts to corresponding platelet counts. It further contains a means for counting electrical pulses greater than the third voltage reference but less than the fourth voltage reference, and comparing such count to a corresponding platelet count.

In addition there is provided an apparatus as described above including fifth and sixth voltage reference means set below said third and fourth voltage reference means, and a means for selectively switching these means for counting the electrical pulses greater than the third voltage reference but less than the fourth to instead count electrical pulses greater than the fifth voltage reference but less than the sixth. This apparatus also has a means for comparing such count to a corresponding platelet count.

FIG. 1 is a perspective view of the housing of the apparatus embodying the present invention;

FIGS. 2A and 2B are schematic diagrams of apparatus embodying the present invention.

FIG. 2C is a valve operating table for FIG. 2B;

FIG. 3 is a cross-sectional view of a portion of the apparatus of FIG. 2A;

FIG. 3A is a cross-sectional view of a portion of FIG. 3, the cross-section being rotated 90° from FIG. 4;

FIG. 4 is a simplified cross-sectional view taken along the line 4—4 of FIG. 3;

FIG. 5 is an equivalent circuit of a portion of FIG. 2A;

FIG. 6 is a block diagram of a signal processing circuit;

FIG. 6A is a detailed circuit of a portion of FIG. 6;

FIG. 7 is a set of curves useful in understanding the invention;

FIG. 8 is a typical whole blood cell distribution curve;

FIG. 9A and 9B are block diagrams illustrating an alarm circuit of the present invention.

FIG. 1 is a perspective view of the laboratory instrument showing a vessel 10 containing a diluted whole blood sample whose platelets are to be counted. A tube $R_S$ extends toward the bottom of vessel 10 for transferring the sample to the instrument.

Figure 10A:
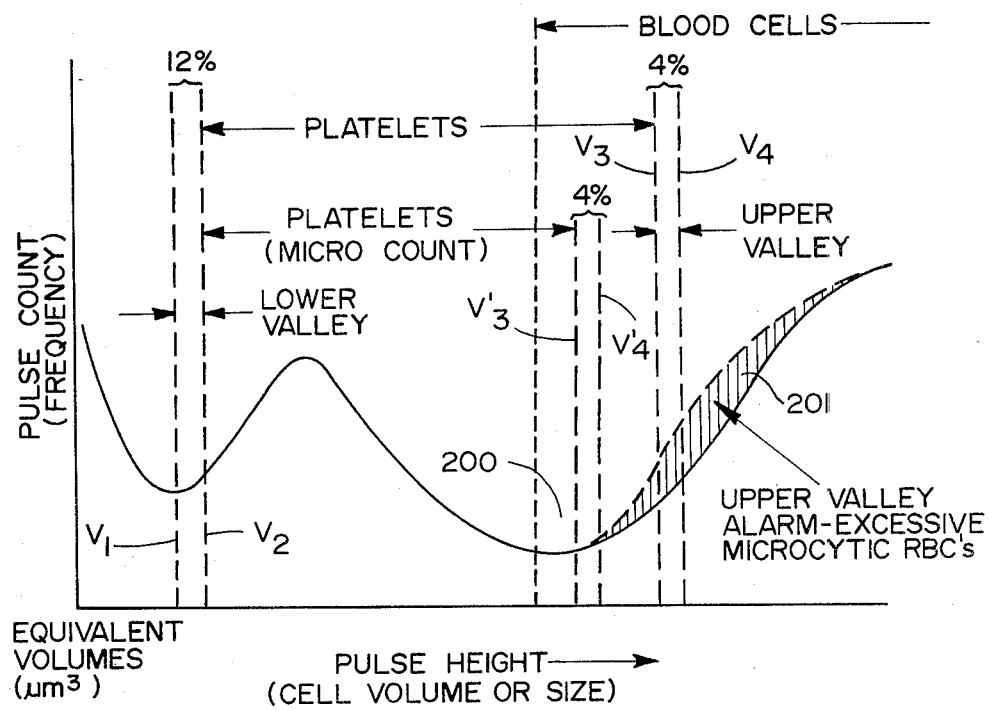
FIGS. 10A and 10B are cell distribution curves illustrating the operation of the above alarm circuit.

Different modes of operation are provided by a rotary switch 9; namely, DRAIN, FILL, FLUSH, RUN and BACK FLUSH. Finally, a set of thumb wheel switches 8 allows for entry of a known red blood cell density. Platelet density is then read out at 71'.

Referring to FIG. 2A, vessel 10 contains a sample of whole blood diluted in a ratio of approximately 1,000:1 which is a liquid suspension of particles including red blood cells and platelets. The blood sample is communicated to an aperture $R_A$ by the small bore tube designated $R_S$, one end of the tube being immersed in the sample and the other end being juxtaposed in close proximity with the aperture (e.g., approximately 30 diameters away from the aperture, the diameter of the aperture being the measurement unit). By means of a tube 11 air is injected into the closed vessel 10 with a pressure of 3 psi to provide a driving or motivating force for causing the sample fluid to flow upwards in the tube $R_S$. Ths sample is injected through the aperture $R_A$ and into an outlet chamber 12 having an opening 13 juxtaposed with the aperture on the opposite side of it as the end of sample tube $R_S$.

A first electrode 14 is immersed in the outlet chamber 12 and has a DC current applied to it which results in an effective 20 volt DC source of voltage and cooperates with a second electrode 16 in accordance with well-known theory to sense the passage of a particle through the aperture $R_A$ and produce a pulse type signal which is indicative of the passage of the particle as well as its size. For example a platelet pulse will be approximately one tenth the size or magnitude of an average red blood cell pulse. By proper threshold discrimination in a signal processing circuit as described in the above Haynes/Shoor patent and as shown in simplified form in FIG. 6 the number of platelets and red blood cells can be concurrently counted in the same sample.

In order to provide for improved hydrodynamic focusing of the passage of particles through the aperture $R_A$ and also to eliminate spurious signals, a front sheath fluid as shown by the arrow 17 (and into which the sample is injected) focuses the sample in its passage through the aperture $R_A$. A back sheath fluid flow 18 on the other side of the aperture aids the passage of the sample and immunizes against spurious signals. The aperture and associated means for facilitating the back sheath and front sheath flows of FIG. 2B is shown in greatly enlarged detail in FIGS. 3 and 4.

In general the particle counter is built around a rectangular block 21 of clear plastic of the polycarbonate type (e.g. LEXAN, a trademark). The transparency of the main building block of the particle counter allows the user to see all important fluid paths and the aperture $R_A$, to check for proper operation e.g., clogging or bubbles. The central portion of block 21 includes a central cylindrical cavity 20 having at its upper portion an outlet chamber 12 and an enlarged diameter lower portion 23 (see FIG. 4). Chambers 33 and 36 are opposed cylindrical cavities in block 21 which are adjacent to cavity 20 and intersect the enlarged cross-section 23.

Chamber 12 is connected to a waste output line 22 and has a catcher tube 12' with its opening 13 opposite and approximately 25 mils from the jewel orifice or aperture $R_A$. Catcher tube 12' is retained by the necked down portion 12" (see FIG. 4) and by a holder 24 inserted into the top of cavity 20, the holder providing the waste outlet 22.

The enlarged lower portion 23 of cavity 20 has inserted in it the holder assembly 26 for the aperture jewel which contains the jewel at the apex of its conical chamber 27 into which the sample tube $R_S$ extends. Since assembly 26 is retained only by the screw-on cap 30 and the O-rings 25 at its other end it is easily removable to allow cleaning of the aperture jewel. Moreover, because the electrode 16 is conveniently located in chamber 33, no electrical connections need be disconnected.

The base or floor 28 of the cone is formed by a holder 29 for the sample tube $R_S$. Near this floor is a fluid passage 31 which extends through the jewel holder 26 for the total sheath fluid and an opposite juxtaposed passage 32 for the back sheath fluid. Passages 31 and 32 are formed by the intersection of chambers 36 and 33 with cavity 20 as shown in FIG. 4. By means of these juxtaposed fluid passages the floor 28 of the conical receptacle 27 is swept clean of debris. The back sheath fluid as indicated by the arrow passes through passage 32 into a chamber 33, which contains the electrode 16 (see FIG. 3A), and then exits this chamber through a back flow fluid resistor R2. R2 is connected to chamber 33 by a coupling 4 and connects the back sheath fluid flow to the chamber 12 by a coupling 5. In back sheath fluid chamber 20 couplings 7 and 6 are for filling and flushing purposes.

Sheath fluid enters a settling chamber 36, included in the block 21, by means of an input coupling 1 connected to a fluid resistor R1. The sheath fluid is particle free saline which has an input pressure of 3 pounds per square inch as it enters R1.

Settling chamber 36 and electrode chamber 33 both are sealed at their top portions by plugs 38 and 39. Alternatively they may be automatic gas bleed films which may, for example, consist of CELGARD, a trademarked material of Celanese Corporation. This material passes gas but blocks liquid because its hydrophobic surface is nonwetting.

Referring now also to FIGS. 2A and 2B the saline particle free fluid for the front and back sheaths is provided by a saline reservoir 41. The saline is driven at an air pressure of 3 psi by the air line input 42 which is connected to an air pump 43 through an air regulator 44. Regulator 44 is also connected via line 46 to the sample vessel 10 and its air input line 11 through a fluid resistor R3. Holder 29, as shown in FIG. 3, forms a spaced collar around tube $R_S$ and air enters this space through the aperture 11' in the collar. Vessel 10 has an upper sleeve type opening 10a which accurately mates with the end of holder 29. Thus the air is efficiently and easily injected into vessel 10. Moreover, vessel 10 contains an exact volume which has been precisely diluted. Fluid resistor R3 is for the purpose of limiting air flow when vessel 10 is removed for refilling. Flow is limited by the fluid resistor R3, which may be constructed of flexible tubing, for example, SILASTIC or TYGON (both trademarks) which has a nominal inner diameter of 0.015 inches and is five inches in length. The approximate flow will be 200 milliliters per minute of air at 3 psi.

The common source of air 43,44 is provided for both the saline reservoir 41 and the sample vessel 10 and by means of saline reservoir 41 the same pressure is present on fluid line 47 which extends through a millipore filter 48 and a flow gauge 49 to the fluid resistor R1. Gauge 49 is used for fault sensing purposes since if the normal flow rate (2 ml/min) changes substantially there is obviously a malfunction. Valve B2 is indicated as being open, i.e., allowing fluid flow. All valves which have an X in the circle are closed to fluid flow and used for filling and other maintenance purposes as shown in the table of FIG. 2C whose five functions correspond to the rotary switch 9 (FIG. 1).

A second open valve, B5, is in series with fluid resistor R2 to allow passage of the back sheath fluid.

Waste on line 22 passes through the open valve B3 and through a drip isolator 51 which is well known in the art and discharges to a waste receptable (not shown). Thus as shown in FIG. 2C in the RUN condition valves B2, B3 and B5 are open allowing fluid flow. The entire transducer structure, valving and fluid resistors are contained within electromagnetic shield 53 and isolated so that no spurious signals interfere with the signal generated on electrodes 14, 16. Waste line 22 is at a +20 volts DC since the saline fluid is a good conductor to the electrode 14 which is connected to the positive terminal of the supply current. Drip isolator 51 isolates this voltage from the shield or other portions of the structure.

FIG. 5 illustrates the fluid resistors and the circulation of both sheath fluid and sample fluid in an equivalent electrical circuit diagram. The 3 psi pressure type driving force is shown as a battery 54. Fluid resistor R1 and the sample tube $R_S$ are connected essentially in parallel to the common source 54 since the 3 psi air source is in effect common as explained. A pressure drop of 0.5 psi is developed across this parallel combination which is essentially provided by the relatively large sheath flow $Q_1$ of approximately 1700 microliters per minute through R1. For the small bore tube $R_S$, $Q_S$ is approximately 35 microliters per minute. Thus the sheath fluid leaving R1 is at a pressure of 2.5 psi, which is the pressure existing in settling chamber 36 and at the end of sample tube $R_S$. Thus as is apparent there is a remaining 2.5 psi pressure drop which occurs across the aperture $R_A$ and the fluid resistor R2, which carries the back sheath fluid and is essentially in parallel with $R_A$. R2 has a fluid flow $Q_2$ of approximately 1,000 microliters per minute at 2.5 psi which is less than the $Q_1$ flow. It is obvious that the difference between $Q_2$ and $Q_1$ is the amount of fluid flow $Q_A$ through the aperture which is 700 microliters per minute at 2.5 psi.

In general the foregoing fluid flows and pressure drops may be analogized to a network problem in Ohm's law where $R_A$ is in parallel with R2 the combination in series with R1 with their "resistive" values being chosen to obtain the desired flows and pressure drops.

The ratio of $Q_A$ to $Q_S$ provides a 20:1 dilution ratio which is in addition to the already 1,000:1 dilution which is present in the sample vessel 10 (FIG. 1).

FIG. 6 is a simplified block diagram of the signal processing circuit to process the pulses of the particle sensing transducer 60 (FIG. 3) and which is claimed and disclosed in greater detail in the above Haynes/Shoor patent. The output of particle sensing transducer 60 is amplified by AC amplifier 61 and has an output 62 connected to a base line restorer circuit 63. The output on line 62 is as illustrated in FIG. 6A the waveshape 62' where the large pulse is a red blood cell and the small pulse a platelet. The output of base line restorer circuit 63 restores the zero DC level as indicated on line 64 and waveform 64'. These particle pulses are then processed to count both red blood cells and platelets.

Specifically an upper threshold detector 66 separates platelets from red blood cells and a lower threshold detector 67 separates platelets from noise. The combination of these two detectors with a peak detector 68 allows the pulse sorter 69 to effectively count and separate out the red blood cell and platelet pulses. Thus a platelet counter 71 counts the platelet pulses and a red blood cell counter 72 the red blood cell (RBC) pulses. As indicated, RBC counter 72 is preset with the known density of the red blood cells of the sample of whole blood being taken by thumb wheel switches 8 (FIG. 1). As discussed in the Haynes/Shoor patent, if red blood cell density is known, then by taking the ratio of RBC counts and platelet counts, platelet density can be obtained. This is effectively done by the circuit of FIG. 6. However, the platelet counter 71, by presetting the red blood cell density in RBC counter 72, will directly readout at 71' (FIG. 1) the platelet density when a stop signal is received in response to RBC counter 72 reaching the preset density count. Since this RBC count must be conducted in the same manner as the previous RBC count upper threshold detector 66 has its threshold set at a somewhat lower level than shown at 64' to include all particles having a size greater than 27.5 cubic microns. This is explained in greater detail in the Haynes/Shoor patent.

In accordance with the present invention a total time test alarm circuit 73 is provided which is responsive to the start of the counting and its stopping. If the test time is less than 12 seconds or greater than 20 seconds a visual alarm 73a indicates a malfunction. Because of the accurate and stable dilution of the blood sample of 20,000:1 and the high repetitive test rate accomplished by the present invention, any test which is outside of the range of 12 to 20 seconds (or other equivalent range time) indicates a malfunction either in the electronic circuit, the fluid circuitry, that the sample is defective or that the preset known RBC density is incorrect. In addition, it might indicate that the sample has some highly abnormal condition because of the number of particles or particle size.

In order to facilitate the high test sample rate capability of the present invention the base restorer circuit 63 as shown in greater detail in FIG. 6A is able to operate at a relatively high repetition rate. In general its purpose is to clamp the baseline of the AC coupled waveform produced by the AC amplifier circuit 61 to approximately zero volts DC thereby making it more convenient to discriminate pulses on the basis of their amplitude. The circuit of FIG. 6A includes a high pass filter circuit having a capacitor 102 and a PNP transistor 103 connected as an emitter follower. It is biased by resistors 104, 105 and 106 and has its emitter output to the noninverting input of an operational amplifier 107. This amplifier serves as a buffer. In operation the common collector configuration of transistor 103 provides a high input resistance to base current flowing toward the base-collector junction and a low resistance to base current flowing away from the junction toward capacitor 102. Thus the capacitor transistor combination provides a DC clamp to zero volts DC. The circuit also serves as a high pass filter eliminating 60 Hz AC current.

With the high sampling rate provided by the present invention, the Poisson sampling error which is $100/\sqrt{N}$ (expressed in %) is relatively low. However, in an aperture type counter as also shown by the curve of FIG. 7 labeled coincidence, as the sampling time increases the frequency of coincidence errors rises. The present invention compensates for this rise by the technique of ratioing the red blood cell count to the platelet count which inherently cancels out coincidence error.

Since platelets are discriminated from noise and red blood cells by their relative pulse heights, it is desirable that there be a relatively clear size valley between, for example, the largest platelets and the smallest red blood cells. The quality of this valley warns of abnormally small red blood cells, abnormally large platelets, or instrument malfunction. Also a second clear valley should occur between noise and the smallest platelets. This serves as a warning of excessive noise, abnormally small or deformed platelets, or instrument malfunction. Where such abnormal platelets are present a noise valley alarm may be an indication of pathological blood.

FIG. 8 is a whole blood cell distribution curve showing lower and upper valleys with the limits $V_1$ and $V_2$ for noise and the normal lower limit of platelet size. The limit $V_3$ is above the normal limit of the largest platelet and is less than the smallest red blood cell. In other words, $V_3$ and $V_4$ are conveniently chosen to provide a range where red blood cells or platelets do not normally occur. Moreover the above limits may be different from the threshold provided by detectors 66 and 67 (FIG. 6) since they are for alarm purposes only. It is obvious that all of the foregoing limits do not have rigid values. This is especially true of $V_1$ where the presence or absence of noise is very relative.

The circuits for implementing the foregoing are illustrated in FIGS. 9A and 9B where a peak hold circuit connected to baseline restorer 63 provides peak voltage $E_p$. A comparator 82 compares noise reference $V_1$ to the baseline input to peak hold circuit 81 to provide a strobe 1 pulse only when $E_p$ is greater than $V_1$. Strobe 1 is used in FIG. 9B to effectively provide a noise reference level.

An upper valley alarm circuit includes comparators 83 and 84 driving the AND gate 86 and NAND gate 87 which at its output 88 has a count of the upper valley pulses. These are counted by divide $N_1$ unit 85, decimal counting units 89 and the sum supplied to a digital comparator 91.

A platelet count is provided through inverter 92, NAND gate 93 and counting units 94 which are also connected to comparator 91. If the valley count is greater than $N_1$% (E.G., 4% as provided by divider 85 where $N_1=4$) of the platelet count, upper valley alarm 96 is illuminated.

Similarly, the lower valley pulses are provided by a comparator 97, NAND gate 98, divide by $N_2$ unit 95, and counting unit 99. A digital comparator 100 makes a similar comparison with the platelet count to illuminate lower valley alarm 101.

In accordance with another embodiment of the invention and still referring to FIG. 9B, a microcytic switch s1 can be installed and be operable from the front panel of the apparatus, which when actuated by the operator to the other position will cause voltage reference levels $V_3'$ and $V_4'$ to be coupled to the amplifiers 83 and 84 rather than $V_3$ and $V_4$. The effect of this change in voltage levels is aptly illustrated in FIGS. 10A and 10B in the valley generally indicated at 200 between the platelet counting range, which has a small-particle population, and the red-blood cell counting range, which has a large-particle population. The new voltage reference levels $V_3'$ and $V_4'$ are between the small-particle population platelets and the original threshold voltage reference levels $V_3$ and $V_4$. When the switch S1 is activated to produce a "microcount" the monitoring region is moved from a location $V_3$, $V_4$ where it is affected by microcytic red blood cells as indicated by the cross-hatched portion 201 to the valley location $V_3'$, $V_4'$, where it is unaffected by microcytic red blood cells. As shown in the drawings, the alarm level is 4% of the maximum of the total platelet count, but it could be a corresponding percentage of the red blood cell count.

Figure 10B:
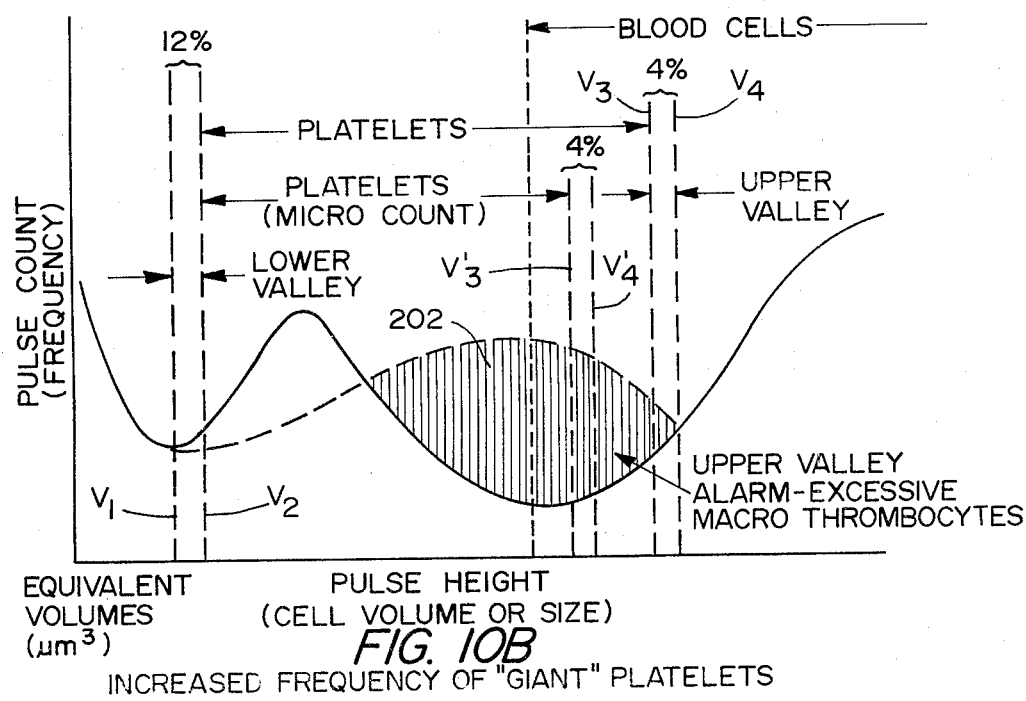

In summary, the use of two different locations in the valley region, as illustrated in FIGS. 10A and 10B, enables the operator to diagnose microcytic red blood cells, since if a sample gives an upper valley alarm, which goes away when the operator switches to the microcytic mode by actuating switch S1, then the alarm is due to excessively small microcytic red blood cells. In practice, if a diagnosis is made of such red blood cells, this means that in the great majority of situations where platelets and red blood cells are being counted, that an accurate count of the platelets will be assured.

With the use of the switch S1, the existence of excessively large platelets, or "macro thrombocytes" can also be established, as shown in FIG. 10B. Here the cross-hatched portion 202 indicates this situation. As is apparent from the diagram, upper valley alarms will occur with switch S1 in either of the positions. Thus, when the alarm persists even in the microcytic mode, the problem is indicated to be excessively large platelets, and the operator is alerted to examine the specimen by microscopic methods.

Finally, in the preferred embodiment, the preferred equivalent volumes (the threshold settings) are the following in cubic micrometers: $V_3$-40; $V_4$-43; $V_3'$-30; $V_4'$-33: and the lower range of red blood cells is at 27.5.

Thus, an improved apparatus for counting particles in a liquid suspension has been provided.

What is claimed is:

1. Apparatus for counting platelets and red blood cells in a sample of blood comprising: means for separately counting platelets and red blood cells of said blood sample including means for sensing their relative sizes by the magnitude of electrical pulses from an aperture type transducer having an assumed noise level, said platelets having normal lower and upper limits of size distribution and said red blood cells having a normal lower limit of size distribution; first voltage reference means set at approximately the upper limit of the assumed noise level of said transducer; second voltage reference means set at approximately the lower limit of normal platelet pulses; third voltage reference means set above the upper limit of normal platelet pulses; fourth voltage reference means set below the lower limit of normal red blood cell pulses; means for counting electrical pulses greater than said first voltage reference but less than said second voltage reference and comparing such count to a corresponding platelet count; means for counting electrical pulses greater than said third voltage reference but less than said fourth voltage reference and comparing such count to a corresponding platelet count.

2. Apparatus as in claim 1 where said means for separately counting platelets and red blood cells includes electrical pulse peak holding means.

3. Apparatus as in claim 1 including alarm means responsive to said comparisons being greater than predetermined percentages.

4. Apparatus for counting particles comprising: means for counting said particles including means for sensing the relative sizes of said particles by the magnitude of electrical pulses from a transducer through which said particles are passed, said transducer having an assumed noise level and said particles having a normal lower limit of size distribution; first voltage reference means set at approximately the upper limits of said assumed noise level; second voltage reference means set at approximately the lower limit of said particle size distribution; means for counting electrical pulses greater than said first voltage reference but less than said second voltage reference and comparing such count to said particle count.

5. Apparatus as in claim 1 including fifth and sixth voltage reference means set below said third and fourth voltage reference means and means for selectively switching said means for counting said electrical pulses greater than said third voltage reference but less than said fourth to instead count said electrical pulses greater than said fifth voltage reference but less than said sixth voltage reference and comparing such count to a corresponding platelet count.

6. Apparatus for counting particles having a relatively large-particle population and a relatively small-particle population, such populations having an intermediate valley region where neither type of particle normally appears comprising: means for separately counting said large and small particles including means for sensing the relative sizes of said particles by the magnitude of electrical pulses from a transducer through which said particles are passed; and means for determining abnormal distributions of said large and small particles including means for monitoring the number of particles in said valley region in at least two different locations and comparing said number with said count of either said large or small particles obtained by said counting means.

7. Apparatus as in claim 6 where said small particles are blood platelets and said large particles are red blood cells.

8. Apparatus as in claim 7 where one of said monitoring locations in said valley region is located to sense excessive microcytic red blood cells and another monitoring location is located so as not to be affected by said microcytic red blood cells.

9. Apparatus as in claim 8 where said another monitoring location is between said one monitoring location and said small-particle population.

* * * * *